United States Patent [19]

Georgiev et al.

[11] Patent Number: 4,777,263

[45] Date of Patent: Oct. 11, 1988

[54] 5-SUBSTITUTED-3-(2-NAPHTHALENYL)-3-((1H-IMIDAZOL-1-YLMETHYL) OR (1H-1,2,4-TRIAZOL-1-YLMETHYL))-2-METHYLISOXAZOLIDINES

[75] Inventors: Vassil S. Georgiev, Penfield; George B. Mullen, Avon, both of N.Y.

[73] Assignee: Pennwalt Corporation, Philadelphia, Pa.

[21] Appl. No.: 104,692

[22] Filed: Oct. 2, 1987

[51] Int. Cl.$^4$ .................. A01N 43/52; A01N 43/653; C07D 233/60; C07D 249/08

[52] U.S. Cl. .................................. 548/240; 548/265; 548/341

[58] Field of Search ........................................ 548/240

[56] References Cited

U.S. PATENT DOCUMENTS

| | | | |
|---|---|---|---|
| 3,709,901 | 1/1973 | Draber et al. | 548/235 |
| 3,711,495 | 1/1973 | Kulsa et al. | 548/240 |
| 3,915,978 | 10/1975 | Kulsa et al. | 548/240 |
| 3,987,179 | 10/1975 | Nadelson | 514/378 |
| 4,010,176 | 3/1977 | Kulsa et al. | 548/242 |
| 4,510,154 | 4/1985 | Yoshida et al. | 514/365 |
| 4,719,306 | 1/1988 | Georgiev | 548/240 |
| 4,723,021 | 2/1988 | Georgiev | 548/240 |

FOREIGN PATENT DOCUMENTS

| | | | |
|---|---|---|---|
| 171137 | 2/1986 | European Pat. Off. | 548/215 |
| 5476579 | 6/1979 | Japan . | |

OTHER PUBLICATIONS

Sokolov, S. V. et al., Chemical Abstract 55:7399 (1961) Abstractin "Isoxazole Compounds III. Synthesis of some isoxazolylazoles", Zhur. Obshchei Khim, 30, pp. 1781–1787 (1960).

Kano, H., et al., Chem. Abstract 62:9139a (1965), Abstracting French 1,376,432 (Oct. 23, 1964).

Kano, H. et al., Chemical Abstract 63:8367a (1965), Abstracting French 1,380,177 (Nov. 27, 1964).

Takahi, Y. et al., Chemical Abstract 81:22233c (1974), Abstracting Japan Kokai 7399,336 (Dec. 15, 1973).

Boyce, C. B. et al., Chemical Abstract 87:23258a (1977), Abstracting German Offen. 2,639,189 (Mar. 10, 1977).

Funaki, Y. et al., Chemical Abstract 92:128915u (1980), Abstracting Japan Kokai 79 76,579 (Jun. 19, 1979).

Kelly, R. C. et al., Chemical Abstract 93:114498u (1980), Abstracting German Offen. 2,918,878 (Nov. 22, 1979).

Haken, P. T. et al., Chemical Abstract 93:132471j (1980), Abstracting Brit, Pat. Appln. 2,024,218 (Jan. 9, 1980).

*Primary Examiner*—Donald G. Daus
*Assistant Examiner*—Mark W. Noel

[57] ABSTRACT

5-Substituted-3-(2-naphthalenyl)-3-[(1H-imidazol-1-ylmethyl or (1H-1,2,4-triazol-1-ylmethyl)]-2-methylisoxazolidines are useful as antifungal agents.

9 Claims, No Drawings

5-SUBSTITUTED-3-(2-NAPHTHALENYL)-3-((1H-IMIDAZOL-1-YLMETHYL) OR (1H-1,2,4-TRIAZOL-1-YLMETHYL))-2-METHYLISOXAZOLIDINES

BACKGROUND OF THE INVENTION

This invention relates generally to substituted 2-methylisoxazolidines and more specifically to 5-substituted-3-(2-naphthalenyl)-3-[(1H-imidazol-1-ylmethyl) or (1H-1,2,4-triazol-1-ylmethyl)]-2-methylisoxazolidines and related derivatives which are useful as antifungal agents.

BRIEF SUMMARY OF THE INVENTION

In accordance with this invention there are provided compounds of the formula:

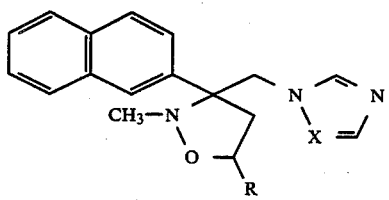

and the pharmaceutically acceptable acid addition salts thereof, in the form of their enantiomers or mixtures of their enantiomers including diastereomeric pairs of such enantiomers, wherein;
  R is selected from phenyl, substituted phenyl, phenoxymethyl, substituted phenoxymethyl, (phenylthio)methyl, substituted (phenylthio)methyl, styryl and $C_2$ to $C_{18}$ alkyl, wherein the substituents on the substituted phenyl rings are selected from one or more of halogen, lower alkyl, lower alkoxy groups and combinations thereof, and
  X is selected from CH or N.

DETAILED DESCRIPTION OF THE INVENTION

The compounds of this invention are useful as antifungal agents. They have in vitro activity against yeast and systemic mycoses and dermatophytes as determined by broth and agar testing techniques [McGinnis, M. R., *Laboratory Handbook of Medical Mycology*, Academic Press, New York, N.Y. (1980)]. The compound prepared in Example 1 was found to have good to moderate inhibitory activity against a variety or organisms including *Trichophyton mentagrophytes, Trichophyton rubrum, Trichophyton tonsurans, Trichophyton schoenleinii, Epidermophyton floccosum, Microsporum canis, Aspergillus fumigatus, Candida albicans* and *Candida stellatoidea* (minimum inhibitory concentration, MIC, of 0.2 to 70 μg/ml).

Because of the antifungal activity of the compounds of the invention they can be used, for example, in suitable liquid, semi-solid or solid carriers in the form of solutions, emulsions, suspensions, dispersions, ointments, aerosols, soaps, detergents, and powders in amounts effective to combat systemic and dermatophylic fungal infections in warm blooded animals (1 to 20 percent active ingredient).

The compounds of this invention are those of the formula:

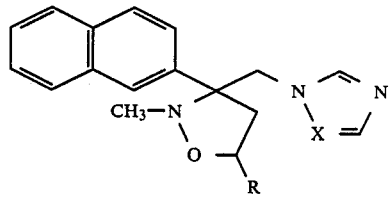

and the pharmaceutically acceptable acid addition salts thereof, in the form of their enantiomers or mixtures of their enantiomers including diastereomeric pairs of such enantiomers, wherein,
  R is selected from phenyl, substituted phenyl, phenoxymethyl, substituted phenoxymethyl, (phenylthio)methyl, substituted (phenylthio)methyl, styryl and $C_2$ to $C_{18}$ alkyl, which can have a branched or unbranched chain. The substituents on the substituted phenyl rings are selected from one or more (and preferably one or two) halogen, lower alkyl, lower alkoxy groups and combinations thereof, and
  X is selected from CH or N.

By halogen is meant chlorine, bromine, fluorine and iodine, with chlorine and fluorine being preferred. By lower alkyl and lower alkoxy is meant groups containing one to six carbons; such groups with three or more carbons can have a branched or unbranched chain.

The 5-substituted-3-(2-naphthalenyl)-3-[(1H-imidazol-1-ylmethyl) or (1H-1,2,4-triazol-1-ylmethyl)]-2-methylisoxazolidines of this invention are obtained as mixtures of cis- and trans-diastereomers due to the presence in the isoxazolidine ring of two asymmetric carbon atoms. The diastereomeric mixture is conveniently separated by flash chromatography on silica gel using halogenated hydrocarbons (preferably dichloromethane and chloroform), alkanols (preferably methanol and ethanol), ethyl acetate and such, as eluents. The eluents may be utilized alone or in combinations, such as the ones comprised of 95-99% by volume halogenated hydrocarbon and 1-5% by volume alkanol. The stereochemistry of the two asymmetric carbon atoms in the isoxazolidine ring may be determined by conventional methods that include x-ray crystallography, nuclear magnetic resonance, circular dichroism and optical rotatory dispersion. Both the cis and trans-diastereomers are resolvable into their optical enantiomers with (+)- and (−)- optical rotations by standard techniques such as fractional recrystallizations of the diastereomeric salts with optically active organic acids, such as (+)- and (−)-tartaric acid, (+)- and (−)-dibenzoyltartaric acid and the like.

As illustrated in the following diagram, the compounds of this invention can be synthesized starting with the reaction of 2-imidazolyl-2'-acetonaphthone (1) with N-methylhydroxylamine hydrochloride to furnish the corresponding nitrone derivative 2. The preparation of such nitrones is described in our copending application Ser. No. 900,856 filed Aug. 27, 1986 whose disclosure is incorporated herein by reference. Subsequent reaction of compound 2 with 1-alkene derivatives provides diastereomeric mixtures of the desired cis- and trans-isoxazolidine compounds 3.

Similarly by using 2-(1H-1,2,4-triazol-1-yl)acetonaphthone the corresponding 3-(1H-1,2,4-triazol-1-ylmethyl)isoxazolidines can be prepared.

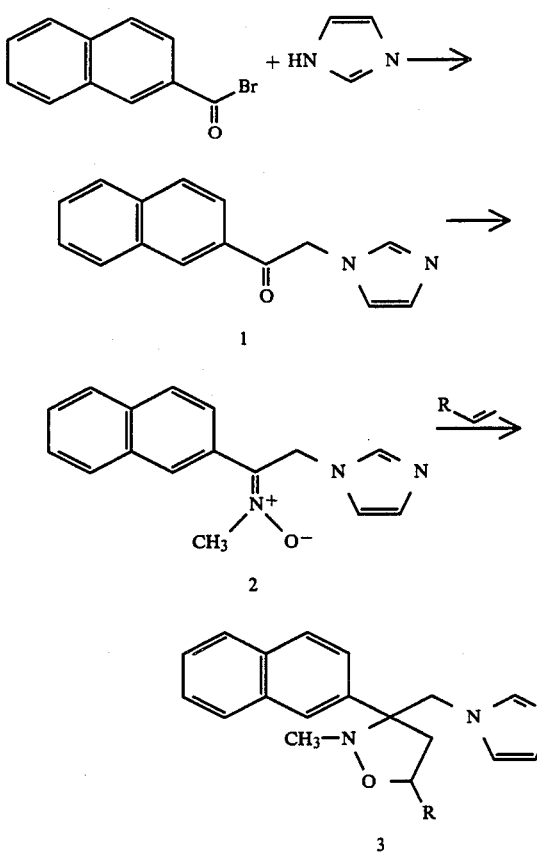

The compounds of this invention are all basic and thus can form salts with pharmaceutically acceptable inorganic and organic acids such as, for example, acetic acid, maleic acid, malic acid, fumaric acid, succinic acid, succinamic acid, tartaric acid, citric acid, lactic acid, hydrochloric acid, hydrobromic acid, hydroiodic acid, nitric acid, sulfuric acid and phosphoric acid.

The preparation of the compounds of this invention is further illustrated by the following synthesis of intermediates and in the Examples.

PREPARATION OF INTERMEDIATES

2-Imidazolyl-2'-acetonaphthone (1)

To a solution of 68.32 g (1.004 mol) of imidazole dissolved in 150 ml of methanol at 0° C. (ice-bath) is added dropwise a solution of 2-bromo-2'-acetonaphthone (50 g, 0.201 mol) in 100 ml of dioxane and 25 ml of ether, while keeping the temperature at 0° C. After about 3 hours at 0° C., the mixture is allowed to warm to room temperature where it is stirred for 20 hours. The mixture is then filtered and added to 500 ml of water, extracted 3 times with 500 ml of chloroform, dried over magnesium sulfate, and evaporated under reduced pressure. The brown oil that remaines is crystallized with a small amount of ethyl acetate and hexane and collected by filtration. The solid is heated in ethyl acetate and filtered hot then concentrated enough to recrystallized the produce as a light tan solid. Yield: 31.07 g (65%); m.p. 125°–126° C. (Found: C, 76.03; H, 5.25; N, 11.81. $C_{15}H_{12}N_2O$ requires: C, 76.25; H, 5.12; N, 11.86).

2-(1H-Imidazol-1-yl)-N-methyl-1-(2-naphthalenyl)ethanimine N-oxide (2)

A mixture of 2-imidazolyl-2'-acetonaphthone (19.63 g, 0.083 mol), N-methylhydroxylamine-HCl (12.50 g, 0.150 mol), and sodium acetate (12.30 g, 0.150 mol), in 500 ml of absolute ethanol is stirred under nitrogen for 72 hours at 25° C. The mixture was filtered, added to water, extracted with chloroform, dried over magnesium sulfate, and evaporated to dryness. The oil that remained is crystallized with a small amount of ethyl acetate and ether. Yield: 14.93 g (68%); m.p. 112°–114° C. (Found:C, 72.14; H, 5.79; N, 15.74. $C_{16}H_{15}N_3O$ requires: C, 72.43; H, 5.70; N, 15.84).

EXAMPLE 1

3-(1H-Imidazol-1-ylmethyl)-2-methyl-3-(2-naphthalenyl)-5-(phenoxymethyl)isoxazolidine (3a) (R=$CH_2OC_6H_5$)

A mixture of compound 2 (9.0 g, 0.034 mol) and phenyl allyl ether (6.98 ml, 0.051 mol) in 200 ml of toluene is refluxed for 48 hours, cooled and evaporated under vacuum. The semisolid that remained (7.30 g, 54%) is crystallized from ether and recrystallized from ethyl acetate to give tan crystals. Yield: 2.4 g (18%); m.p. 176°–178° C. (Found: C, 74.96; H, 6.41; N, 10.40. $C_{25}H_{25}N_3O_2$ requires: C, 75.16; H, 6.31; N, 10.52).

EXAMPLE 2

The following derivatives are prepared by a procedure similar to that described for derivatives 3a:
5-[(4-Chlorophenoxy)methyl]-3-(1H-imidazol-1-ylmethyl)-2-methyl-3-(2-naphthalenyl)isoxazolidine (3b) (R=$CH_2OC_6H_4Cl$-p)

Derivative 3b is prepared from compound 2 and p-chlorophenyl allyl ether, and is recrystallized from ethyl acetate/hexane. Yield: 31%; m.p. 163°–165° C. (Found: C, 69.15; H, 5.73; N, 9.60; Cl, 8.08. $C_{25}H_{24}N_3O_2Cl$ requires: C, 69.20; H, 5.57; N, 9.68; Cl, 8.17).

3-(1H-Imidazol-1-ylmethyl)-2-methyl-3-(2-naphthalenyl)-5-phenylisoxazolidine (3c) (R=phenyl)

Derivative 3c is prepared from compound 2 and styrene and is recrystallized from ethyl acetate. Yield: 31%; m.p. 170°–172° C. (Found: C, 77.95; H, 6.59; N, 11.31. $C_{24}H_{23}N_3O$ requires: C, 78.02; H. 6.26; N, 11.37).
5-(4-Chlorophenyl)-3-(1H-imidazol-1-ylmethyl)-2-methyl-3-(2-naphthalenyl)isoxazolidine (3d) (R=$C_6H_4Cl$-p)

Derivative 3d is prepared from compound 2 and p-chlorostyrene and is recrystallized from ethyl acetate. Yield: 38%; m.p. 195°–198° C. (Found: C, 71.16; H, 5.57; N, 10.32; Cl, 8.90 $C_{24}H_{22}N_3OCl$ requires: C, 71.37; H, 5.49; N, 10.40; Cl, 8.78.
5-Hexyl-3-(1H-imidazol-1-ylmethyl)-2-methyl-3-(2-naphthalenyl)isoxazolidine (3e) [R=$(CH_2)_5CH_3$]

Derivative 3e is prepared from compound 2 and 1-octene. Purification of 3e is done by flash chromatography on silica gel with eluent comprised of 98% chloroform and 2% ethanol by volume. The compound is crystallized with ether/hexane. Yield: 12%; m.p. 92°–94° C. (Found: C, 75.98; H, 8.17; N, 10.96; $C_{24}H_{31}N_3O$ requires: C, 76.36; H, 8.28; N, 11.13).

EXAMPLE 3

3-(1H-Imidazol-1-ylmethyl)-5-[(4-methoxyphenoxy)methyl]-2-methyl-3-(2-naphthalenyl)isoxazolidine (3f) (R=$CH_3OC_6H_4OCH_3$-p)

A mixture of compound 2 (13.0 g, 0.049 mol) and p-methoxyphenyl allyl ether (12.07 g, 0.073 mol) in 400 ml of toluene is refluxed for 48 hours, cooled, and the solvent removed in vacuo leaving a dark oil. Chloroform is added to the oil and carbon is added to decolorize the solution which is filtered through a bed of celite. The chloroform is evaporated and the oil that remained is purified by flash chromatography on silica gel (eluent comprised of 98% CHCl₃ and 2% MeOH). The resulting tan solid (5.56 g, 26%) is recrystallized from ethyl acetate, m.p. 143°–145° C. (Found: C, 72.58; H, 6.46; N, 9.66. $C_{26}H_{27}N_3O_3$ requires: C, 72.71; H, 6.34; N, 9.78).

EXAMPLE 4

3-(1H-Imidazol-1-ylmethyl)-2-methyl-3-(2-naphthalenyl)-5-(2-trans-phenylethenyl)isoxazolidine     (3g)
(R=CH=CHC₆H₅)

A mixture of compound 2 (11.02 g, 0.042 mol) and trans-1-phenyl-1,3-butadiene (8.0 g, 0.062 mol) in 500 ml of toluene is heated to 85° C. and held there for 72 hours, cooled and evaporated to dryness. The oil that remained is purified by flash chromatography on silica gel (eluent comprised of 98% CHCl₃ and 2% MeOH by volume). The resulting semisolid is dissolved in chloroform, decolorized with carbon, and filtered through a bed of celite. The solvent is evaporated and the resulting tan solid recrystallized from ethyl acetate/hexane, m.p. 166°–169° C. (Found: C, 78.68; H, 6.39; N, 10.60. $C_{26}H_{25}N_3O$ requires: C, 78.96; H, 6.37; N, 10.62).

EXAMPLE 5

2-Methyl-3-(2-naphthalenyl)-5-(2-trans-phenylethenyl)-3-(1H-1,2,4-triazol-1-ylmethyl)isoxazolidine     (3f)
(R=CH=CHC₆H₅, X=N)

A mixture of 2-(1H-1,2,4-triazol-1-yl)-N-methyl-1-(2-naphthalenyl)ethanimine N-oxide (15.0 g, 0.056 mol) and trans-1-phenyl-1,3-butadiene (11.0 g, 0.084 mol) in 500 ml toluene is heated to 95°–105° C. for 48 hours, then cooled and evaporated to dryness. The resulting oil is decolorized with carbon and purified by flash chromatography on silica gel (eluent comprised of 90% ethyl acetate and 10% hexane by volume) giving two diastereomers. Isomer A (5.66 g) has a melting point of 80°–84° C. (ethyl acetate-pentane). Isomer B (1.64 g) has a melting point 157°–160° C.

EXAMPLE 6

5-Substituted-3-(2-naphthalenyl)-3-(1H-imidazol-1-ylmethyl)-2-methylisoxazolidines By following essentially the same procedures as described for Example 3 and replacing p-methoxyphenyl allyl ether by
(a) allyl 4-methylphenyl sulfide, or
(b) allyl phenyl sulfide,
the corresponding 5-substituted-3-(2-naphthalenyl)-3-(1H-imidazol-1-ylmethyl)-2-methylisoxazolidines can be prepared. For example,
5-{[(4-methylphenyl)thio]methyl}-3-(2-naphthalenyl)-3-(1H-imidazol-1-ylmethyl)-2-methylisoxazoldine,
5-[(phenylthio)methyl]-3-(2-naphthalenyl)-3-(1H-imidazol-1-ylmethyl)-2-methylisoxazolidine.

EXAMPLE 7

5-Substituted-3-(2-naphthalenyl)-3-(1H-1,2,4-triazol-1-ylmethyl)-2-methylisoxazolidines (X=N)

By following essentially the same procedures as described for Example 5 and replacing trans-1-phenyl-1,3-butadiene by
(a) 4-chlorostyrene, or
(b) allyl 4-methylphenyl sulfide, or
(c) allyl phenyl ether, or
(d) allyl 4-methoxyphenyl ether, or
(e) allyl 4-chlorophenyl ether, or
(f) 1-octene, the corresponding 5-substituted-3-(2-naphthalenyl)-3-(1H-1,2,4-triazol-1-ylmethyl)-2-methylisoxazolidines can be prepared.

2-methyl-3-(2-naphthalenyl)-5-(4-chlorophenyl)-3-(1H-1,2,4-triazol-1-ylmethyl)isoxazolidine,
5-[(phenylthio)methyl]-2-methyl-3-(2-naphthalenyl)-3-(1H-1,2,4-triazol-1-ylmethyl)isoxazolidine,
2-methyl-3-(2-naphthalenyl)-5-(phenoxymethyl)-3-(1H-1,2,4-triazol-1-ylmethyl)isoxazolidine,
5-[(4-chlorophenoxy)methyl]-2-methyl-3-(2-naphthalenyl)-3-(1H-1,2,4-triazol-1-ylmethyl)isoxazolidine,
5-[(4-methoxyphenoxy)methyl]-2-methyl-3-(2-naphthalenyl)-3-(1H-1,2,4-triazol-1-ylmethyl)isoxazolidine,
5-hexyl-2-methyl-3-(2-naphthalenyl)-3-(1H-1,2,4-triazol-1-ylmethyl)isoxazolidine.

Salts of the compounds of the invention can be prepared as known in the art, for example, by dissolving the compound in a 10:1 by volume mixture of ethanol and aqueous acid such as HCl or HNO₃, evaporating the solvent, and then recrystallizing the crude salt, for example, from methanol-ether, 1:3 by volume in the case of HCl salts, and ethanol in the case of HNO₃ salts.

We claim:

1. A compound of the formula:

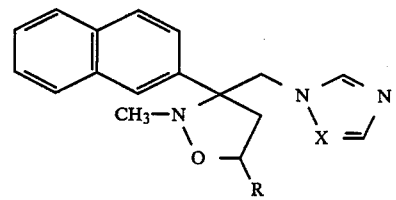

and the pharmaceutically acceptable acid addition salts thereof, in the form of their enantiomers or mixtures of their enantiomers including diastereomeric pairs of such enantiomers, wherein;

R is selected from phenyl, substituted phenyl, phenoxymethyl, substituted phenoxymethyl, (phenylthio)methyl, substituted (phenylthio)methyl, styryl and $C_2$ and $C_{18}$ alkyl, wherein the substituents on the substituted phenyl rings are selected from one to three of halogen, lower alkyl, lower alkoxy groups and combinations thereof, and X is selected from CH or N.

2. The compound of claim 1 wherein the compound is 3-(1H-imidazol-1-ylmethyl)-2-methyl-3-(2-naphthalenyl)-5-(phenoxymethyl)isoxazolidine.

3. The compound of claim 1 wherein the compound is 5-[(4-chlorophenoxy)methyl]-3-(1H-imidazol-1-ylmethyl)-2-methyl-3-(2-naphthalenyl)isoxazolidine.

4. The compound of claim 1 wherein the compound is 3-(1H-imidazol-1-ylmethyl)-2-methyl-3-(2-naphthalenyl)-5-phenylisoxazolidine.

5. The compound of claim 1 wherein the compound is 5-(4-chlorophenyl)-3-(3H-imidazol-1-ylmethyl-3-(2-naphthalenyl)isoxazolidine.

6. The compound of claim 1 wherein the compound is 5-hexyl-3-(1H-imidazol-1-ylmethyl)-2-methyl-3-(2-naphthalenyl)isoxazolidine.

7. The compound of claim 1 wherein the compound is 3-(1H-imidazol-1-ylmethyl)-5-[(4-methoxyphenoxy)methyl]-2-methyl-3-(2-naphthalenyl)isoxazolidine.

8. The compound of claim 1 wherein the compound is 3-(1H-imidazol-1-ylmethyl)-2-methyl-3-(2-naphthalenyl)-5-(2-trans-phenylethenyl)isoxazolidine.

9. The compound of claim 1 wherein the compound is 2-methyl-3-(2-naphthalenyl)-5-(2-trans-phenylethenyl)-3-(1H-1,2,4-triazol-1-ylmethyl)isoxazolidine.

* * * * *